(12) United States Patent
Shang et al.

(10) Patent No.: US 12,303,600 B2
(45) Date of Patent: May 20, 2025

(54) MAGNETIC ASSISTED DRUG DELIVERY

(71) Applicants: Hao Shang, Irvine, CA (US); Damacia Zhimei Shang, Irvine, CA (US)

(72) Inventors: Hao Shang, Irvine, CA (US); Damacia Zhimei Shang, Irvine, CA (US)

( * ) Notice: Subject to any disclaimer, the term of this patent is extended or adjusted under 35 U.S.C. 154(b) by 516 days.

(21) Appl. No.: 16/888,355

(22) Filed: May 29, 2020

(65) Prior Publication Data

US 2020/0375900 A1 Dec. 3, 2020

Related U.S. Application Data

(60) Provisional application No. 62/856,047, filed on Jun. 1, 2019.

(51) Int. Cl.
*A61K 9/14* (2006.01)
*A61K 9/00* (2006.01)
*A61K 45/06* (2006.01)
*A61M 25/00* (2006.01)

(52) U.S. Cl.
CPC .............. *A61K 9/14* (2013.01); *A61K 9/0019* (2013.01); *A61K 45/06* (2013.01); *A61M 25/0043* (2013.01); *A61M 2025/0057* (2013.01); *A61M 2205/0272* (2013.01); *A61M 2210/12* (2013.01)

(58) Field of Classification Search
CPC .... A61B 17/12022; A61B 2017/00876; A61B 17/1214; A61K 49/5094
See application file for complete search history.

(56) References Cited

U.S. PATENT DOCUMENTS

| | | | |
|---|---|---|---|
| 5,236,410 A * | 8/1993 | Granov | A61M 37/0092 600/12 |
| 5,549,915 A | 8/1996 | Volkmfsky et al. | |
| 5,648,124 A | 7/1997 | Sutor et al. | |
| 5,921,244 A | 7/1999 | Chen et al. | |
| 6,355,275 B1 * | 3/2002 | Klein | A61P 15/00 424/9.4 |
| 8,227,262 B2 | 7/2012 | Fonnum et al. | |
| 8,273,324 B2 | 9/2012 | Rioux et al. | |
| 8,316,862 B2 | 11/2012 | Shapiro et al. | |
| 8,900,293 B2 | 12/2014 | Forbes et al. | |
| 2004/0136905 A1 * | 7/2004 | Kent | A61K 9/0009 424/646 |
| 2006/0204442 A1 | 9/2006 | Tapolsky et al. | |
| 2011/0196474 A1 | 8/2011 | Davalian et al. | |
| 2012/0095442 A1 * | 4/2012 | Dormer | A61K 9/0009 604/507 |

FOREIGN PATENT DOCUMENTS

| | | | |
|---|---|---|---|
| WO | WO-2006075185 | 7/2006 | |
| WO | WO-2015168062 A1 * | 11/2015 | A61M 25/10 |

OTHER PUBLICATIONS

Goodwin, Scott C., et al. "Single-dose toxicity study of hepatic intra-arterial infusion of doxorubicin coupled to a novel magnetically targeted drug carrier." Toxicological sciences 60.1 (2001): 177-183.

Alexiou, Christoph, et al. "Locoregional cancer treatment with magnetic drug targeting." Cancer research 60.23 (2000): 6641-6648.

Alexiou, Christoph, et al. "Magnetic drug targeting: biodistribution and dependency on magnetic field strength." Journal of Magnetism and Magnetic Materials 252 (2002): 363-366.

Lübbe, Andreas Stephan, et al. "Clinical experiences with magnetic drug targeting: a phase I study with 4'-epidoxorubicin in 14 patients with advanced solid tumors." Cancer research 56.20 (1996): 4686-4693.

* cited by examiner

*Primary Examiner* — Micah Paul Young
(74) *Attorney, Agent, or Firm* — Mannava & Kang, P.C.

(57) ABSTRACT

A method of delivering magnetic particles to a target site, including inserting a magnet catheter into a blood vessel; advancing the magnet catheter to a position downstream from the target site; and releasing magnetic particles into the blood vessel upstream of the target site; in which a first portion of the magnetic particles embolize in the blood vessel is disclosed. A system is also disclosed.

18 Claims, 7 Drawing Sheets

MAGNETIC ASSISTED DRUG DELIVERY

RELATED APPLICATION

The present application claims priority to U.S. Provisional Application No. 62/856,047, filed Jun. 1, 2019, the entire disclosure of which is hereby incorporated by reference.

FIELD OF THE INVENTION

The present invention relates to a method of delivering magnetic particles to a target site, including inserting a magnet catheter into a blood vessel; advancing the magnet catheter to a position downstream from the target site; and releasing magnetic particles into the blood vessel upstream of the target site; in which a first portion of the magnetic particles embolize in the blood vessel. A system for performing the method is also disclosed.

BACKGROUND OF THE INVENTION

There are over one million cases of cancer diagnosed each year in the United States and numerous approaches of therapy including systemic chemotherapy, radiation and surgical resection have been applied to treat cancers. Given that systemic chemotherapy and radiation interact with healthy tissue, complications and toxicity often result. Ablative approaches, including microwave, radiofrequency and cryogenic therapies have been used; however, these methods are often not selective and tissues and organs surrounding the tumor can be affected.

It has long been proposed to target the delivery of a substance within the human body by encapsulating the substance within magnetic particles (for example, magnetite particles) and use magnetic fields and/or gradients to concentrate the particles close to a magnet for delivery of the substance. For example, it has been proposed to deliver an antitumor substance to a tumor by coating magnetite particles with the substance, introducing the particles into the patient's blood stream, and guiding the coated magnetite particles to the tumor site with a magnet. It has also been proposed to physically absorb a therapeutic substance to magnetic particles, concentrate the magnetic particles at a tumor with a magnet, and de-absorb the therapeutic substance.

The movement of a magnetic particle is controlled by the magnetic force from the magnet and the hydrodynamic force from the blood flow. The magnetic force can concentrate the magnetic particles at the target site while the hydrodynamic force can disperse the particles into the circulatory system. However, due to the fast decay of a magnetic field with distance, the magnetic force is often not sufficient to overcome the hydrodynamic force associated with blood flow in the circulatory system unless the particles are close to the magnet. In addition, the magnitude of hydrodynamic force varies widely, due to the large disparity in blood velocities ranging from less than 0.1 cm/s in capillaries to over 1 m/s in large blood vessels.

Two approaches have been proposed previously to apply a magnetic force. The first is to use a strong external magnet placed outside of the human body and close to the target site. The magnetic field is effective when the target site is close to the body surface, usually within a few centimeters, such that the magnetic field can overcome the hydrodynamic forces. As a result, the application of this approach is limited. The second approach is to use an internal magnet that is attached to a catheter, which is delivered to the vicinity of the target site to attract and concentrate the magnetic particles locally. However, due to the small size of the magnet, this approach requires the magnetic particles to be close to the magnet so that the magnetic particles can be attracted and concentrated. As a result, a certain percentage of magnetic particles are carried away by the blood flow into the circulatory system.

Transarterial chemoembolization (TACE) is another target delivery of therapeutic substance to a target site. In this approach embolic agents, such as micron size particles, mixed with a therapeutic substance are injected directly into the tumor blood vessel using a catheter. Embolization therapy blocks the blood vessel and causes a shutdown of blood flow to the target site and simultaneously the drug is released locally. A radioactive agent, such as yttrium-90 (y90), is also used, rather than chemical drugs, as the therapeutic substance. The TACE procedures are usually performed by inserting a small catheter into the artery and navigating it into the blood vessel close to the target site. This approach relies on normal blood flow as the means by which the embolic agent moves into the tumor and systolic pressure as the packing force. However, the blood vessel structure is complex, especially for the hyper-vascularized tumor site. The blood flow direction is difficult to predict. As a result, part of the embolic agent may not enter the tumor site, but enter the general circulatory system, with a concomitant risk of delivery of the substance to organs that can be damaged by the toxic substance. In the case of particle TACE, the particles need to be in the micron scale so that the particles can get into the blood vessel of the target where the therapeutic substance is released to have effective therapeutic effect. However, due to the complex hydrodynamics of blood flow, particularly within the cancer tumor, it is difficult to contain the particles at the target site. When the particles enter the general circulatory system, they can embolize the blood vessels in other organs and cause serious consequences, such as stroke.

The particles can escape from the treatment site due to the complex blood vessel structure of the treatment site. Once released from the catheter, the particles can be carried by the blood into the blood vessels around the treatment site, as oppose to going into the treatment site. Thus, these particles can bypass the target site and enter the general circulatory system. In another scenario, when small size particles are carried into the blood vessel of the target site the chance is increased that the particles can not be trapped in the blood vessel of the target site due to their small size. A fraction of the particles can flow through the target site and enter into the general circulatory system. In both scenarios, the particles can escape from the target site.

SUMMARY OF THE INVENTION

In an aspect, there is disclosed a method of delivering magnetic particles to a target site, including inserting a magnet catheter into a blood vessel; advancing the magnet catheter to a position downstream from the target site; and releasing magnetic particles into the blood vessel upstream of the target site; in which a first portion of the magnetic particles embolize in the blood vessel.

In another aspect, there is also disclosed a system for providing a therapeutic substance to a target site comprising: a magnet, a magnet catheter for delivering the magnet; a plurality of magnetic particles associated with a therapeutic substance; and a delivery catheter for delivering the plurality of magnetic particles.

BRIEF DESCRIPTION OF THE DRAWINGS

The present disclosure in its several aspects and embodiments can be more fully understood from the detailed description and the accompanying drawings, wherein.

Throughout this specification and figures like reference numbers identify like elements.

DETAILED DESCRIPTION OF THE INVENTION

It is to be understood that both the foregoing general description and the following detailed description are exemplary and explanatory only, and are intended to provide an explanation of various embodiments of the present teachings. The layers/components shown in each Figure may be described with regard to a particular Figure, but it is understood that the description of a particular layer/component would be applicable to the equivalent layer/component in the other Figures.

The present application is directed to a method of delivering magnetic particles to a target site, comprising: inserting a magnet catheter into a blood vessel; advancing the magnet catheter to the blood vessel downstream from the target site; releasing magnetic particles into the blood vessel upstream of the target site; and removing the magnet catheter and the magnetic particles after the magnetic particles attach to the magnet catheter.

Figure 1:
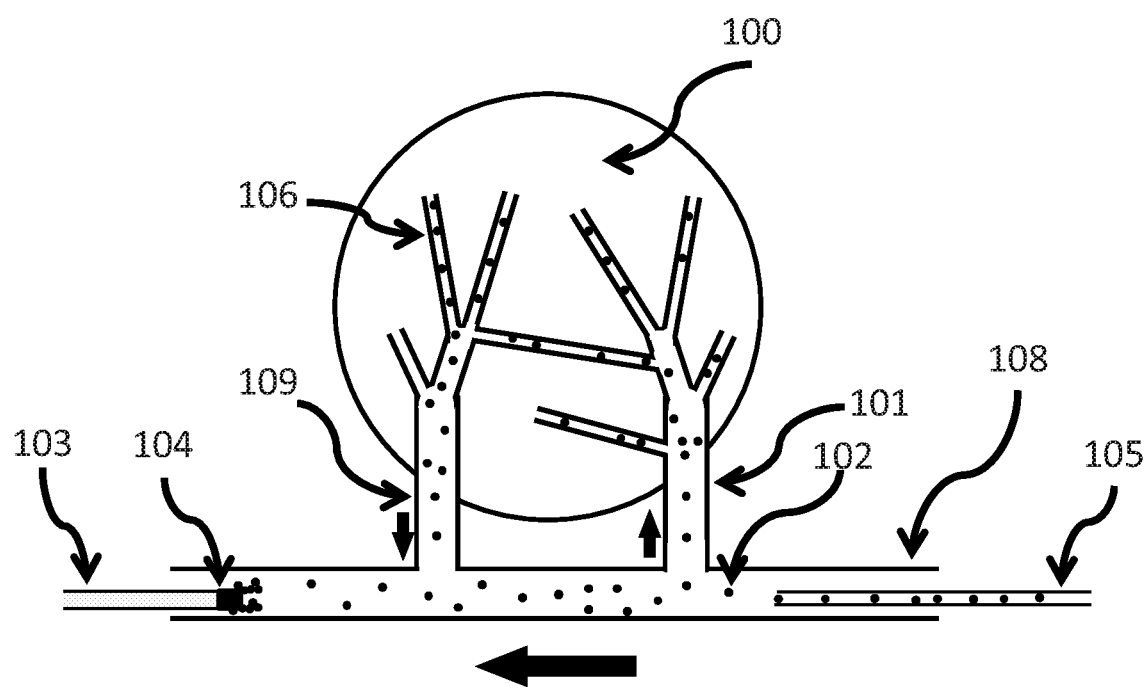
FIG. 1 illustrates a magnet catheter positioned downstream from a target site and magnetic particles inserted upstream of a target site.

Referring to FIG. 1, a magnet catheter 103 with a magnet 104 can be inserted into a blood vessel 108. The magnet catheter 103 can be advanced to a position downstream from a target site 100. A delivery catheter 105 can be inserted into a blood vessel 108 and advanced to a position upstream from the target site 100. The blood vessel 108 can bifurcate to supply blood to the target site 100. The arrows indicate the direction of the blood flow. Magnetic particles 102 can be released from the delivery catheter 105, then can be carried by the blood flow into the target site 100 via bifurcated blood vessel 101. In an aspect, a first portion of the magnetic particles 102 can embolize in a blood vessel 106 within the target site 100. For example, the blood vessel 106 within the target site can have a diameter that is less than an average particle size of the magnetic particles 102. In this manner, the first portion of the magnetic particles 102 can embolize the blood vessel 106 within the target site. The first portion can be 100% of the total amount of the magnetic particles 102 released into the blood vessel 108, for example, can be less than 100% of the total amount, and as a further example, can be less than 90% of the total amount, based upon the total amount of the magnetic particles 102 released.

In another aspect, a second portion of magnetic particles 102, which do not embolize within a blood vessel within the target site, can attach to a magnet 104 of the magnet catheter 103. The second portion of magnetic particles 102 may not embolize within the blood vessel within the target site for a few reasons, such as the blood vessel diameter is larger than the average particle size of the magnetic particles 102. Moreover, the magnetic particles 102 may not enter the blood vessel within the target site 100 due to a bifurcated blood vessel upstream of the target site. To be clear, a second portion of magnetic particles 102 can flow through the target site 100 or do not enter the target site 100 and can attach to the magnet 104. The second portion can be 100% of the total amount of the magnetic particles 102 released into the blood vessel 108, for example, can be less than 100% of the total amount, and as a further example, can be less than 90% of the total amount, based upon the total amount of the magnetic particles 102 released.

The magnet catheter 103 can be any delivery device including one or more magnets. The magnet 104 can be any type that can generate a magnetic field suitable for attracting the magnetic particles. Non-limiting examples of magnets 104 suitable for use in the magnet catheter include neodymium iron boron (NdFeB), samarium cobalt (SmCo), alnico (aluminum, nickel, cobalt alloy), ceramic magnets, and ferrite magnets. In an aspect, the magnet 104 for use in the magnet catheter 103 can be a permanent magnet. In another aspect, the magnet 104 for use in the magnet catheter 103 can be an electromagnet. In an aspect, the method can include varying an electric current supplied to the magnet catheter 103 to adjust a magnetic field. The electrical current can be supplied via conductive wires in the magnet catheter connected to an external power source. A flexible magnet 104 made with a composite of resin and magnetic powder can also be used.

Figure 2A:
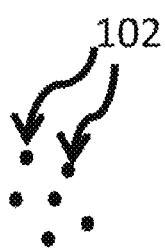
FIG. 2a illustrates a plurality of magnetic particles.
Figure 2B:
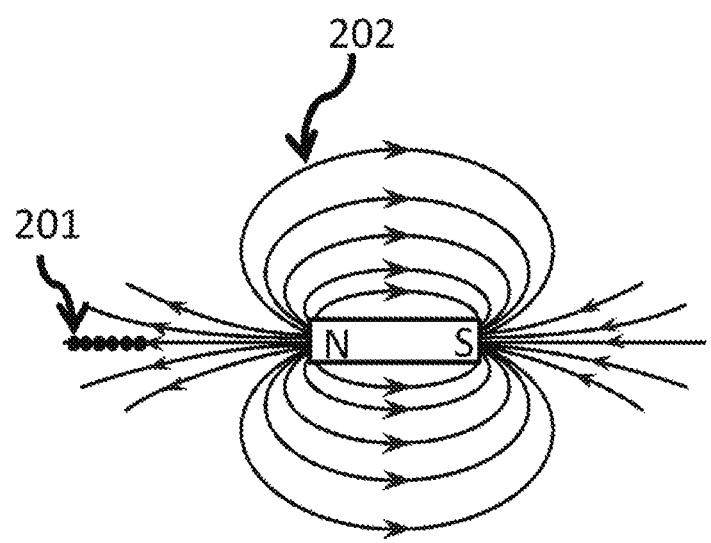
FIG. 2b illustrates the plurality of magnetic particles in an aggregate form under the influence of a magnetic field.

In an aspect, the magnet 104 can be selected to generate a magnetic field with a small magnetic field intensity. For example, the magnet 104 should not generate a magnetic field that can cause the magnetic particles 102 to form aggregates within a blood vessel before entering the target site. FIG. 2a illustrates magnetic particles 102. Referring now to FIG. 2b, the magnetic particles 102 can form aggregates 201 in a magnetic field 202, for example, with a high magnetic field intensity. The aggregates 201 can be large thereby making it difficult to flow through a blood vessel to the target site.

As used herein, the term "blood vessel" includes an artery, an arteriole, a capillary, a vein, and a venule. As used herein, the term "upstream" refers to a location of a blood vessel in which blood flows towards the target site. As used herein, the term "downstream" refers to a location of a blood vessel in which blood flows away from the target site. A target site can be any site in a body in need of treatment. In an aspect, the target site can be an area of tissue, such as a tumor, a polyp, fibroids, etc. In another aspect, the target site can be a blood vessel, such as varicose veins.

A delivery catheter 105 can include magnetic particles 102. The delivery catheter 105 can be any type of delivery device so long as it can enter a blood vessel 108 and can deliver magnetic particles 102. The magnetic particles 102 can be in any shape, such as spherical, oblong, elliptical, needle-like, etc. The magnetic particles 102 can be any material that can be magnetized by a magnetic field, such as a magnetic field generated by a magnet 104 of the magnet catheter 103. The magnetic particles 102 can be paramagnetic, superparamagnetic, or ferromagnetic.

In an aspect, the magnetic particles 102 can be associated with a therapeutic substance. For example, the magnetic particles 102 can include a magnetic material, a biodegradable polymer, and a therapeutic substance. In an aspect, the therapeutic substance and/or the magnetic material can be encapsulated by the polymer material so that the therapeutic substance is released over time at the target site 100.

In another aspect, the therapeutic substance can be absorbed to a surface of the magnetic particle 102 via the biodegradable polymer.

In another aspect, a radiopaque material can be included in the magnetic particle so that the magnetic particle can exhibit enhanced visibility under x-ray fluoroscopy such as during the administration of the magnetic particle.

Non-limiting examples of radiopaque material include metal, such as tungsten, tantalum, platinum, palladium, lead, gold, titanium, silver, mixtures and alloys thereof; a metal oxide, such as titanium oxide, zirconium oxide, and aluminum oxide; bismuth subcarbonate; barium sulfate; and combinations thereof.

Non-limiting examples of suitable magnetic material include materials that can be magnetized by a magnetic field, such as iron oxides (magnetite ($Fe_3O_4$), maghemite ($Fe_2O_3$)), iron, iron containing alloy (such as martensitic stainless steel), neodymium iron boron, nickel, nickel containing compound (such as AlNiCo), cobalt, cobalt containing compound (such as $SmCo_5$), mixtures or alloys thereof.

Non-limiting examples of a biodegradable polymer include poly (ε-caprolactone), poly (butylene succinate), poly [(butylene succinate)-co-adipate], poly(butylene adipate-co-terephthalate), aliphatic polyester, aliphatic-aromatic co-polyesters, poly (lactic acid), polylactide, polyglycolic acid, polysaccharides, collagen, chitosan, starch, poly (hydroxybutyrate), pH sensitive biodegradable polymer, and combinations thereof.

Non-limiting examples of a therapeutic substance include an anti-tumor drug, such as doxorubicin, Adriamycin, BiCNU, Carboplatinum, Daunorubicin, DTIC, Fludarabine, Gemcitabine, Idarubicin, Irinotecan, Mithramycin, Mitomycin, Mitoxantrone, Navelbine, Nitrogen Mustard, Taxol, Taxotere, Topotecan, Velban, Vincristine, VP-16; radionuclides with a covalently bound chelator e.g. DPTA or DOTA; photodynamic therapy drugs, such as Phthalocyanines, Gene Vectors which may be bound to a covalently bound chelator (e.g. Streptavadin); Tumor Necrosis Factors; Clot busting drugs, such as Alteplase or TPA (brand name: ACTIVASE), Streptokinase (Streptase or Kabikinase), Urokinase (Abbokinase), Anistreplase (Eminase), Reteplase (Retavase); Steroids; Antibiotics; Tumor necrosis agents; antiangiogenesis agents; and combinations thereof. Other non-limiting examples of therapeutic substance that can be used include adrenocortical steroid; adrenocortical suppressant; aldosterone antagonist; amino acids; anabolics; anthelmintic; anti-acne agent; anti-adrenergic; anti-allergic:anti-amebic; anti-androgen; anti-anemic; anti-anginal; antiarthritic; antiasthmatic; anti-atherosclerotic; antibacterial; anticholelithic; anticholelithogenic; anticholinergic; anticoagulant; anticoccidal; antidiabetic; antidiarrheal; antidiuretic; antidote; antiestrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimitotic; antimycotic, antineoplastic, antineutropenic, antiparasitic; antiperistaltic, antipneumocystic; antiproliferative; antiprostatic hypertrophy; antiprotozoal; antipruritic; antipsoriatic; antirheumatic; antischistosomal; antiseborrheic; antisecretory; antispasmodic; antithrombotic; antitussive; anti-ulcerative; antiurolithic; antiviral; appetite suppressant; benign prostatic hyperplasia therapy agent, bone resorption inhibitor; bronchodilator, carbonic anhydrase inhibitor, cardiac depressant; cardioprotectant; cardiotonic; cardiovascular agent; choleretic; cholinergic; cholinergic agonist; cholinesterase deactivator, coccidiostat; diagnostic aid; diuretic; ectoparasiticide; enzyme inhibitor, estrogen; fibrinolytic; free oxygen radical scavenger; glucocorticoid; gonad-stimulating principle; hair growth stimulant; hemostatic; hormone; hypocholesterolemic; hypoglycemic; hypolipidemic; hypotensive; immunizing agent; immunomodulator; immunoregulator, immunostimulant; immunosuppressant; impotence therapy adjunct; inhibitor, keratolytic: LHRH agonist; liver disorder treatment, luteolysin; mucolytic, mydriatic; nasal decongestant; neuromuscular blocking agent; non-hormonal sterolderivative; oxytocic; plasminogen activator, platelet activating factor antagonist, platelet aggregation inhibitor, potentiator, progestin, prostaglandin; prostate growth inhibitor; prothyrotropin; pulmonary surface; radioactive agent; regulator, relaxant; repartitioning agent; scabicide: sclerosingagent; selective adenosine A1 antagonist; Steroid; symptomatic multiple sclerosis; synergist; thyroid hormone; thyroid inhibitor; thyromimetic; amyotrophic lateral sclerosis agents; paget's disease agents; unstable angina agents; uricosuric; vasoconstrictor; vasodilator, vulnerary; wound healing agent; xanthine oxidase inhibitor, and mixtures thereof.

Figure 3:
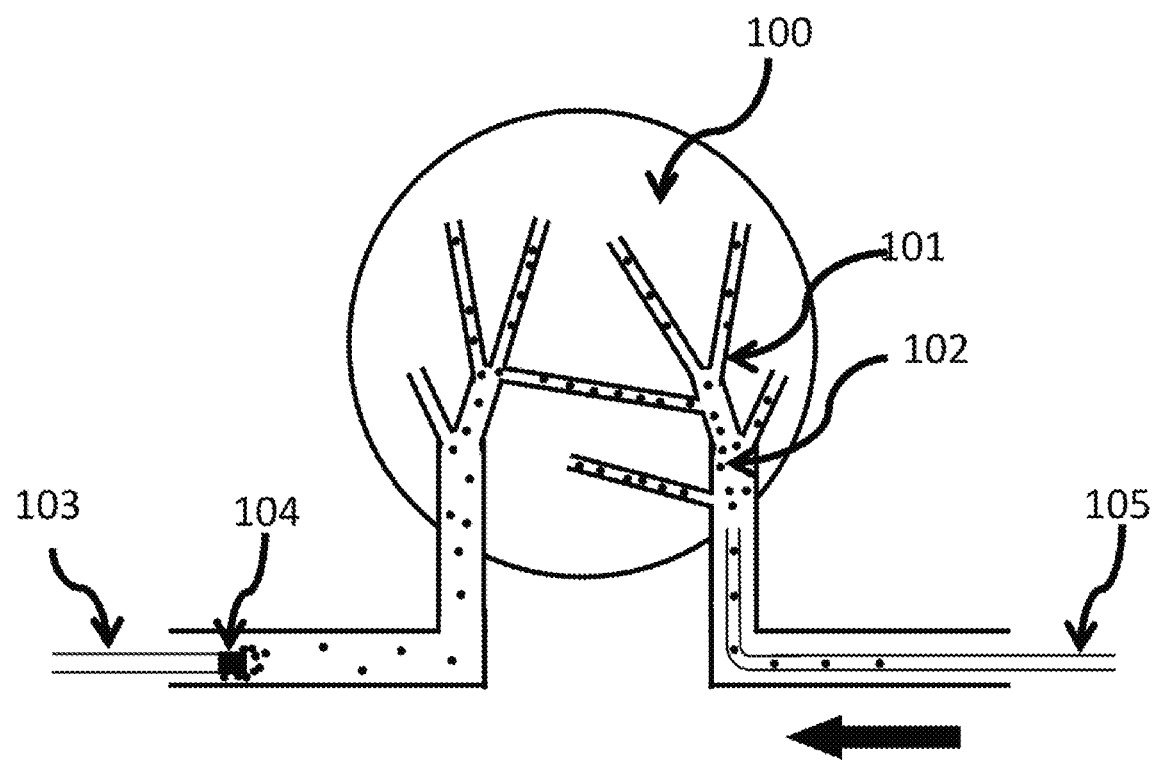
FIG. 3 illustrates a magnet catheter and magnetic particles downstream from the target site.

Referring to FIG. 3, a magnet catheter 103 can be inserted into a blood vessel located downstream from a target site 100. Magnetic particles 102 can be released from a delivery catheter 105 upstream from the target site 100. A first portion of the magnetic particles 102 can embolize in the blood vessel of the target site 100. A therapeutic substance associated with magnetic particles 102 can be released at the target site 100. A second portion of the magnetic particles 102 can flow through the target site 100 and can be attracted by magnet 104 and collected on the magnet catheter 103 for removal. It should be noted that the blood vessel of the target site 100 can vary significantly and be much more complex than illustrated in FIG. 3.

Figure 4:
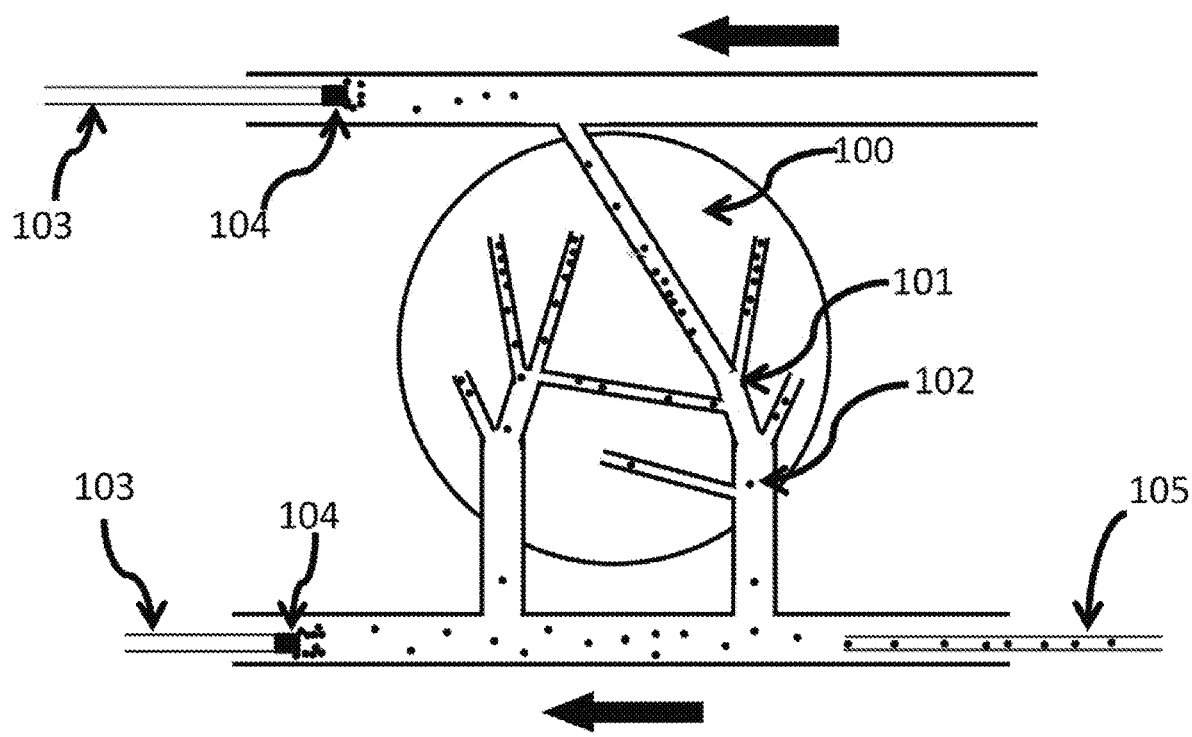
FIG. 4 illustrates multiple magnet catheters located in multiple blood vessels that can attract magnetic particles from the target site.

Referring to FIG. 4, a plurality of magnet catheters 103 can be inserted into a plurality of blood vessels. For example, a first magnet catheter 103 can be inserted into a first blood vessel located downstream from a target site 100, and a second magnet catheter 103 can be inserted into a second blood vessel located downstream from a target site 100. When a plurality of magnet catheters 103 are used, they can be positioned a certain distance apart from one another so that the magnets 104 associated with each magnet catheter 103 are not attracted to each other. The distance depends on the magnet size and the magnetic strength of the magnet material.

Figure 5:
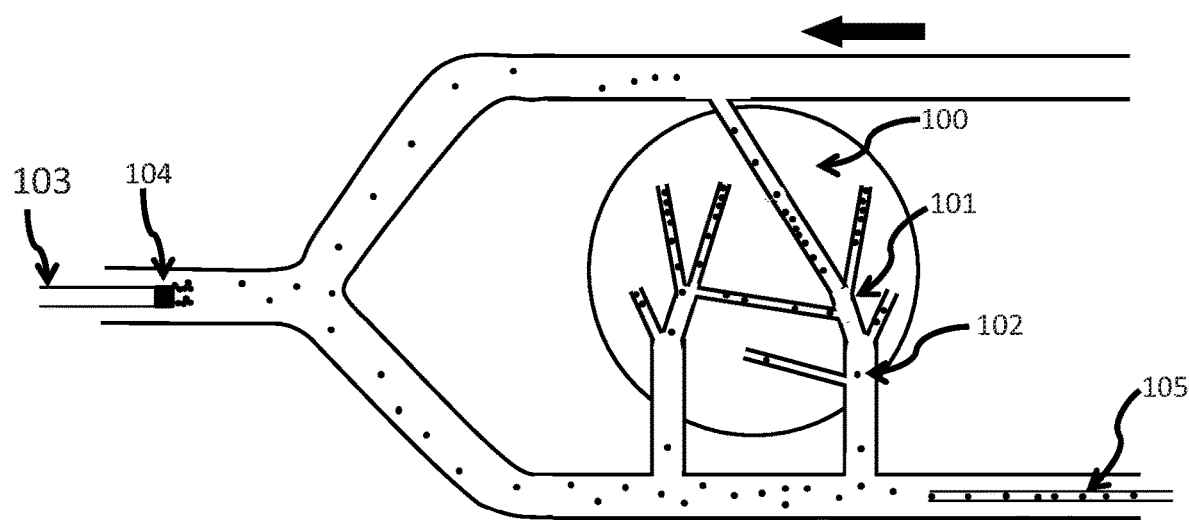
FIG. 5 illustrates a magnet catheter in a converging downstream blood vessel.

In FIG. 5, a magnet catheter 103 can be placed in a blood vessel that is a convergence from two blood vessels of the target site 100. The magnetic particles 102 that are not embolized in the target site 100 can be captured by the magnet 104.

Figure 6:
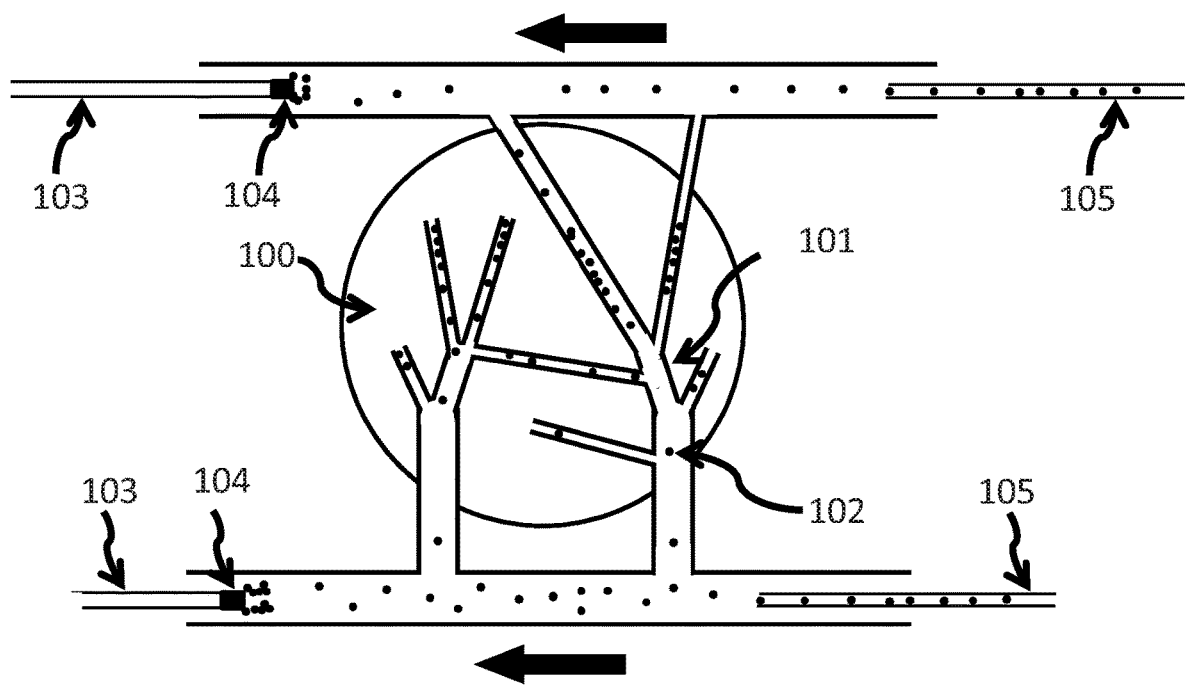
FIG. 6 illustrates multiple magnet catheters in multiple blood vessels and magnetic particles.

In FIG. 6, a plurality of delivery catheters 105, each including magnetic particles 102, can be inserted into a plurality of blood vessels upstream of a target site 100. For example, a first delivery catheter 105 can be inserted into a first blood vessel located upstream from a target site 100, and a second delivery catheter 105 can be inserted into a second blood vessel located upstream from the target site 100.

Figure 7:
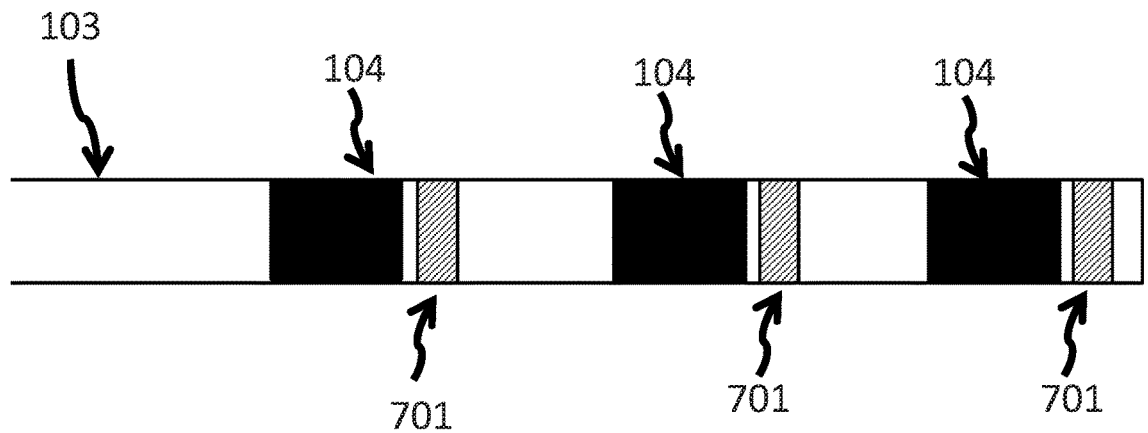
FIG. 7 illustrates a plurality of magnets on one magnet catheter.
Figure 8:
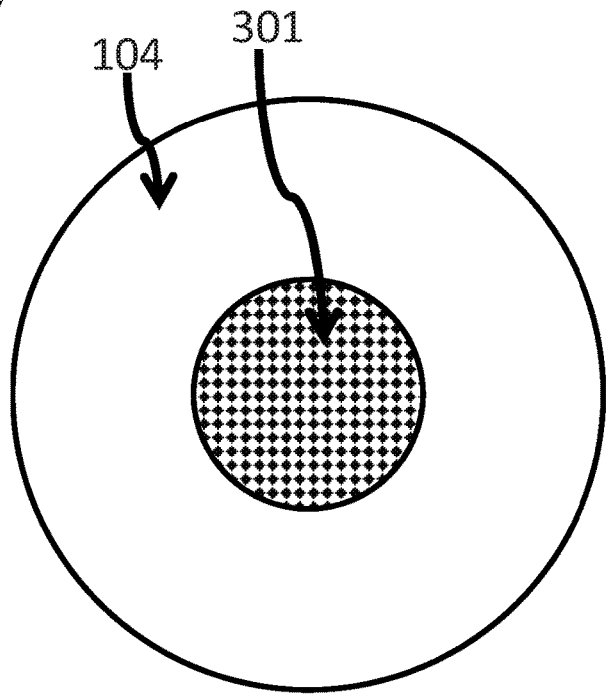
FIG. 8 illustrates a cross-section of the magnet catheter.

In FIG. 7, a plurality of magnets 104 can be attached to a magnet catheter 103. A radiopaque marker 701 can be placed close to the magnet to show the position of the magnet under x-ray fluoroscopy. FIG. 8 Illustrates a magnet 104 attached on an outside of a core 301 of the magnet catheter 103. The method can also include a step of removing the magnet catheter 103, magnets 104, and attached magnetic particles 102 from the downstream blood vessel. As a result, the amount of magnetic particles and the encapsulated substance are reduced in the general circulatory system.

There is also disclosed a system for providing a therapeutic substance to a target site comprising: a magnet, a magnet catheter for delivering the magnet; a plurality of magnetic particles associated with a therapeutic substance; and a delivery catheter for delivering the plurality of magnetic particles. The components of the system are as described above. From the foregoing description, those skilled in the art can appreciate that the present teachings can be implemented in a variety of forms. Therefore, while these teachings have been described in connection with particular embodiments and examples thereof, the true scope of the present teachings should not be so limited. Various changes and modifications can be made without departing from the scope of the teachings herein.

This scope disclosure is to be broadly construed. It is intended that this disclosure discloses equivalents, means, systems and methods to achieve the devices, activities and mechanical actions disclosed herein. For each device, article, method, mean, mechanical element or mechanism disclosed, it is intended that this disclosure also encompasses in its disclosure and teaches equivalents, means, systems and methods for practicing the many aspects, mechanisms and devices disclosed herein. Additionally, this disclosure regards a method and its many aspects, features and elements. Such a method can be dynamic in its use and operation, this disclosure is intended to encompass the equivalents, means, systems and methods of the use of a device and/or catheter and its many aspects consistent with the description and spirit of the operations and functions disclosed herein. The claims of this application are likewise to be broadly construed. The description of the inventions herein in their many embodiments is merely exemplary in nature and, thus, variations that do not depart from the gist of the invention are intended to be within the scope of the invention. Such variations are not to be regarded as a departure from the spirit and scope of the invention.

What is claimed is:

1. A method of delivering magnetic particles to a target site, comprising:
   inserting a magnet catheter including one or more magnets into a blood vessel;
   advancing the magnet catheter to a position downstream from the target site; and
   releasing magnetic particles into the blood vessel upstream of the target site;
   wherein a first portion of the magnetic particles embolize in the blood vessel; and
   wherein a second portion of the magnetic particles attach to a magnet of the magnet catheter and do not embolize within a blood vessel.

2. The method of claim 1, wherein the magnet catheter includes a permanent magnet.

3. The method of claim 1, wherein the magnet catheter includes an electromagnet.

4. The method of claim 1, wherein the target site is chosen from a tumor, a varicose vein, a polyp, and a fibroid.

5. The method of claim 1, wherein the magnetic particles are associated with a therapeutic substance.

6. The method of claim 5, wherein the therapeutic substance is an anti-tumor drug.

7. The method of claim 1, wherein the magnetic particle includes a magnetic material, a biodegradable polymer, and a therapeutic substance.

8. The method of claim 7, wherein the therapeutic substance is encapsulated by the biodegradable polymer.

9. The method of claim 5, wherein the therapeutic substance is absorbed to a surface of the magnetic particle.

10. The method of claim 1, wherein the step of inserting the magnet catheter includes inserting a plurality of magnet catheters into a plurality of blood vessels.

11. The method of claim 10, wherein the plurality of magnet catheters are positioned a distance apart from one another.

12. The method of claim 1, wherein releasing magnetic particles includes inserting a delivery catheter into a blood vessel upstream of the target site and releasing magnetic particles associated with the delivery catheter.

13. The method of claim 12, wherein the delivery catheter can be a plurality of delivery catheters.

14. The method of claim 1, wherein the step of releasing magnetic particles includes inserting a plurality of delivery catheters into a plurality of blood vessels.

15. The method of claim 1, wherein the magnet catheter and the attached magnetic particles are removed.

16. The method of claim 1, wherein an average particle size of the first portion of magnetic particles is larger than a diameter of the blood vessel.

17. The method of claim 3, further comprising a step of varying an electric current supplied to the magnet catheter to adjust a magnetic field strength.

18. A method of delivering magnetic particles to a target site, comprising:
   inserting a magnet catheter including one or more magnets into a blood vessel;
   advancing the magnet catheter to a position downstream from the target site;
   releasing magnetic particles into the blood vessel upstream of the target site, a first portion of the magnetic particles embolizing in a blood vessel within the target site and a second portion of the magnetic particles attaching to a magnet of the magnet catheter, the second portion of magnetic particles not embolizing within a blood vessel; and
   removing the magnet catheter with the second portion of magnetic particles; wherein the blood vessel within the target site has a diameter that is less than an average particle size of the magnetic particles.

* * * * *